(12) United States Patent
Boden et al.

(10) Patent No.: US 6,610,647 B2
(45) Date of Patent: Aug. 26, 2003

(54) FRAGRANCE MOLECULE

(75) Inventors: Richard M. Boden, Ocean, NJ (US); Charles E. J. Beck, Summit, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 126 days.

(21) Appl. No.: 09/992,299

(22) Filed: Nov. 14, 2001

(65) Prior Publication Data

US 2002/0055454 A1 May 9, 2002

Related U.S. Application Data

(63) Continuation-in-part of application No. 09/638,402, filed on Aug. 15, 2000.

(51) Int. Cl.$^7$ .................................................. A61K 7/46
(52) U.S. Cl. ................................. 512/12; 512/1; 512/8; 512/11; 512/25
(58) Field of Search ............................ 512/1, 8, 11, 12, 512/25

(56) References Cited

U.S. PATENT DOCUMENTS

| | | |
|---|---|---|
| 4,335,097 A | 6/1982 | David et al. |
| 4,534,891 A | 8/1985 | Boden et al. |
| 5,334,581 A | 8/1994 | Behan et al. |
| 5,399,353 A | 3/1995 | Bartnik et al. |
| 5,518,712 A | 5/1996 | Stewart |

OTHER PUBLICATIONS

The Merck Index, S. Budavari, er., Merck & Co., Rahway, NJ, 1989, pp. 6,7,1321.

*Primary Examiner*—Jill Warden
*Assistant Examiner*—Monique T. Cole
(74) *Attorney, Agent, or Firm*—Joseph F. Leightner

(57) ABSTRACT

The present invention is directed to the use of insoluble acesulfame in creating fragrances and scents in such items as perfumes, colognes, toilet waters, cleaning products and personal care products.

7 Claims, No Drawings

FRAGRANCE MOLECULE

This is a Continuation-in-Part (CIP) of prior application Ser. No. 09/638,402, filed Aug. 15, 2000.

FIELD OF THE INVENTION

The present invention relates to use of acesulfame in a fragrance formulation.

BACKGROUND OF THE INVENTION

Acesulfame, often referred to as acesulfame K, is a well-known sweetener that has been used to sweeten food products for many years. Acesulfame is relatively water insoluble, so acesulfame is often used in its salt form in food products. The salt forms commonly employed include sodium, calcium, potassium, magnesium salts. The most common salt of acesulfame used in foods, is the potassium salt, hence acesulfame K.

While these salts have been used in food products for many years, acesulfame is odorless. Therefore acesulfame was not thought to be suitable for incorporation into fragrances.

In the fragrance industry there is ongoing need to develop new compounds to give perfumers and other persons in the art the ability to create new fragrances for perfumes, air fresheners, candles, colognes and personal care products.

SUMMARY OF THE INVENTION

The present invention is a method of imparting, enhancing or modifying a fragrance by the addition of an olfactory acceptable amount of insoluble acesulfame. The fragrance can be used to provide a fragrance to various articles such as cologne, toilet water, perfume, air freshener, candles or personal care products.

DETAILED DESCRIPTION OF THE INVENTION

The present invention is based upon the surprising discovery that the incorporation of an olfactory effective amount of insoluble acesulfame in fragrances enhances the fragrance perceived by the user. This is surprising because acesulfame is odorless. The incorporation of insoluble acesulfame has been found to add a heightened awareness of the fragrance to the consumer. This heightened awareness of the fragrance to the consumer is compared to fragrances that did not include the insoluble acesulfame in the fragrance formulation. The inclusion of the insoluble acesulfame creates a fragrance that is more perceptible or recognizable at lower levels to the consumer. In addition, the insoluble acesulfame provides enhanced notes at the same level or modifies the fragrance by providing a sweetness to the fragrance which is not present when the insoluble acesulfame is not present.

As noted above, the food industry commonly employs acesulfame salts as sweeteners in aqueous materials, such as beverages. The present invention employs acesulfame in its insoluble form, the non-salt form, in the fragrance.

The use of the this compound is widely applicable in current perfumery products, including the preparation of perfumes and colognes, the perfuming of personal care products, such as soaps, shower gels, bath and body oils and hair care products as well as air fresheners, candles and cosmetic preparations. The present invention can also be used to perfume cleaning agents, such as, but not limited to detergents, dishwashing materials, scrubbing compositions, window cleaners and the like.

In these preparations, the compound of the present invention can be used alone or in combination with other perfuming compositions, solvents, adjuvants and the like. The nature and variety of the other ingredients are known by those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal scents, such as woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in their entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Olfactory effective amount is understood to mean the amount of compound in perfume compositions the individual component will contribute its particular olfactory characteristics, but the olfactory effect of the perfume composition will be the sum of the effects of each of the perfume or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of insoluble acesulfame used in the invention employed in the perfumed article varies widely from about 0.001 to about 0.5 weight percent. In a preferred embodiment, the level is from 0.05 to about 0.45 and most preferably from about 0.1 to about 0.4 weight percent. In addition to these compounds, other agents can be used in conjunction with the fragrance. Well known materials such as surfactants, emulsifiers, and polymers used to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 10 weight percent of the perfumed composition, preferably from about 0.1 to about 5 and most preferably from about 0.2 to about 1 weight percent. Those with skill in the art will be able to employ the desired level of the compounds of the invention to provide the desired fragrance and intensity.

The following are provided as specific embodiments of the present invention. Other modifications of this invention will be apparent to those skilled in the art without departing from the scope of this invention. As used herein all percentages are weight percent and g is understood to be grams. All of the materials employed in the examples are available from International Flavors & Fragrances Inc., Hazlet, N.J.

EXAMPLE 1

A peach fragrance was made incorporating acesulfame using the formulation set forth below.

| | |
|---|---|
| Acet C-6 (n-hexyl acetate) | 2.5 |
| Benzyl acetate | 1.0 |
| Cassis ether | 2.5 |
| Gamma decalactone | 12.0 |
| Gamma dodecalalactone | 2.0 |
| Iso-propyl myristate | 973.4 |
| acesulfame (insoluble) | 0.5 |

The fragrance was described as having a peach-like fragrance with fruity notes.

Comparative Example 1

The fragrance of Example 1 was reproduced, however the acesulfame was not included. The fragrance did not have the same intensity as the fragrance that included the acesulfame.

EXAMPLE 2

An apple fragrance was made incorporating saccharin using the formulation set forth below.

| | |
|---|---|
| Acet C-6 (n-hexyl acetate) | 5.0 |
| Damascenone | 1.0 |
| Geranyl propionate | 1.0 |
| Fragarone | 1.0 |
| Iso-propyl myristate | 987.6 |
| Manzanate | 0.5 |
| acesulfame (insoluble) | 0.5 |

The fragrance was described as having an apple-like fragrance with fruity notes.

Comparative Example 2

The fragrance of Example 2 was reproduced, however, the acesulfame was not included. The fragrance did not have the same intensity as the fragrance that included the acesulfame.

What is claimed is:

1. A method of imparting, enhancing or modifying a fragrance by the addition of an olfactory acceptable amount of insoluble acesulfame.

2. The method of claim 1 wherein the fragrance is incorporated into perfumes, colognes, cleaning agents, toilet water and personal care products.

3. The method of claim 2 wherein the cleaning agent is selected from the group consisting of detergents, dishwashing materials, scrubbing compositions, and window cleaners.

4. The method of claim 2 wherein the level of insoluble acesulfame is from about 0.001 to about 0.5 weight percent.

5. The method of claim 3 wherein the level of insoluble acesulfame is from about 0.05 to about 0.45 weight percent.

6. The method of claim 4 wherein the level of insoluble acesulfame is from about 0.1 to about 4 weight percent.

7. The method of claim 1 wherein the level of insoluble acesulfame is about 0.5 weight percent.

* * * * *